(12) United States Patent
Mizumachi et al.

(10) Patent No.: US 9,877,460 B2
(45) Date of Patent: Jan. 30, 2018

(54) ANIMAL URINARY FUNCTION MEASURING DEVICE AND ANIMAL URINARY FUNCTION MEASURING METHOD

(75) Inventors: Ryoji Mizumachi, Tokyo (JP); Hiroaki Fukuda, Tokyo (JP)

(73) Assignee: LSI MEDIENCE CORPORATION, Tokyo (JP)

( * ) Notice: Subject to any disclaimer, the term of this patent is extended or adjusted under 35 U.S.C. 154(b) by 0 days.

(21) Appl. No.: 13/390,233

(22) PCT Filed: Aug. 12, 2010

(86) PCT No.: PCT/JP2010/063690
§ 371 (c)(1),
(2), (4) Date: Feb. 13, 2012

(87) PCT Pub. No.: WO2011/019068
PCT Pub. Date: Feb. 17, 2011

(65) Prior Publication Data
US 2012/0137758 A1    Jun. 7, 2012

(30) Foreign Application Priority Data

Aug. 12, 2009 (JP) .................................. 2009-187420

(51) Int. Cl.
*G01N 33/493*   (2006.01)
*A01K 1/03*     (2006.01)
(Continued)

(52) U.S. Cl.
CPC ............ *A01K 1/031* (2013.01); *A01K 23/005* (2013.01); *A61B 10/007* (2013.01)

(58) Field of Classification Search
CPC ..... A01K 1/031; A01K 23/005; A61B 10/007
See application file for complete search history.

(56) References Cited

U.S. PATENT DOCUMENTS 3,063,413 A * 11/1962 Fuller et al. ................... 119/417
3,107,650 A * 10/1963 Cass .............................. 119/417
(Continued)

FOREIGN PATENT DOCUMENTS

CN    2152388    1/1994
CN    2591958    12/2003
(Continued)

OTHER PUBLICATIONS

JP2006226919 Nakayama et al. English translation.*
(Continued)

*Primary Examiner* — Paul West
*Assistant Examiner* — Xin Zhong
(74) *Attorney, Agent, or Firm* — Wenderoth, Lind & Ponack, L.L.P.

(57) ABSTRACT

It is an object of the present invention to provide an animal urinary function measuring device and an animal urinary function measuring method each with high accuracy in sampling a urine amount of an animal. There are provided an accommodating portion which accommodates an animal other than humans, a collecting portion which is provided below the accommodating portion and collects urine discharged by the animal in the accommodating portion, a reticulated portion which is provided below the accommodating portion, allows the passage of the urine of the animal into the collecting portion, collects an object other than the urine, and whose wire diameter of a net thereof being not more than 0.5 mm and whose mesh size being not less than 1 mm² and not more than the maximum mesh size determined by at least one of the excrement of the animal accommodated in the accommodating portion and a predetermined object used to accommodate the animal in the accommodating portion, a measuring portion which measures the weight of the urine collected by the collecting (Continued)

portion, and a data recording portion which records data measured by the measuring portion.

13 Claims, 16 Drawing Sheets

(51) Int. Cl.
 *A01K 23/00* (2006.01)
 *A61B 10/00* (2006.01)

(56) References Cited

U.S. PATENT DOCUMENTS

| | | | | |
|---|---|---|---|---|
| 4,154,196 | A | * | 5/1979 | Gass ............................ 119/417 |
| 5,596,948 | A | * | 1/1997 | Ritchie .................. A01K 1/031 |
| | | | | 119/417 |
| 5,807,278 | A | * | 9/1998 | McRae .................. A61B 5/205 |
| | | | | 600/573 |
| 6,234,115 | B1 | * | 5/2001 | Blum et al. .................... 119/472 |

FOREIGN PATENT DOCUMENTS

| | | | |
|---|---|---|---|
| CN | 201146735 | | 11/2008 |
| EP | 0 749 685 | | 12/1996 |
| JP | 61-67543 | | 5/1986 |
| JP | 62-94759 | | 6/1987 |
| JP | 5-27673 | | 4/1993 |
| JP | 9-322670 | | 12/1997 |
| JP | 09322670 A | * | 12/1997 |
| JP | 10-150876 | | 6/1998 |
| JP | 2002-365283 | | 12/2002 |
| JP | 2002365283 A | * | 12/2002 |
| JP | 2006-226919 | | 8/2006 |
| JP | 2006226919 A | * | 8/2006 |

OTHER PUBLICATIONS

JP 09322670 Okuma, Hachiro English translation.*
JP 2002365283 Hashimoto, Tadatoshi English translation.*
JP 2006226919 English translation.*
JP 09322670 English translation.*
JP 2002365283 English translation.*
Chinese Office Action along with English translation dated Jul. 2, 2013 in corresponding Chinese application No. 201080035864.7.
International Preliminary Report on Patentability dated Mar. 22, 2012 in International (PCT) Application No. PCT/JP2010/063690.
Extended European Search Report dated Dec. 20, 2013 in corresponding European Patent Application No. 10808251.2.
Notice of Reasons for Rejection, with English translation, dated Dec. 10, 2013 in corresponding Japanese Patent Application No. 2011-526784.
Office Action dated Feb. 25, 2014, in corresponding Chinese Application No. 201080035864.7 with English translation.
Final Decision of Rejection dated Sep. 16, 2014 in corresponding Japanese application No. 2011-526784 (with English translation).
Notice of Re-examination dated Apr. 20, 2016, in Chinese Application No. 201080035864.7 (with English translation).
European Office Action dated Apr. 22, 2016, in European Patent Application No. 10808251.2.
Appeal Decision dated Nov. 4, 2016 with English translation issued in the corresponding Chinese application No. 201080035864.7.
Decision of Rejection dated May 21, 2015 in Chinese Application No. 201080035864.7, with translation.
Notice of Submission of Opinion dated Dec. 13, 2016 in corresponding Korean Application No. 10-2012-7006039, with English translation.

* cited by examiner

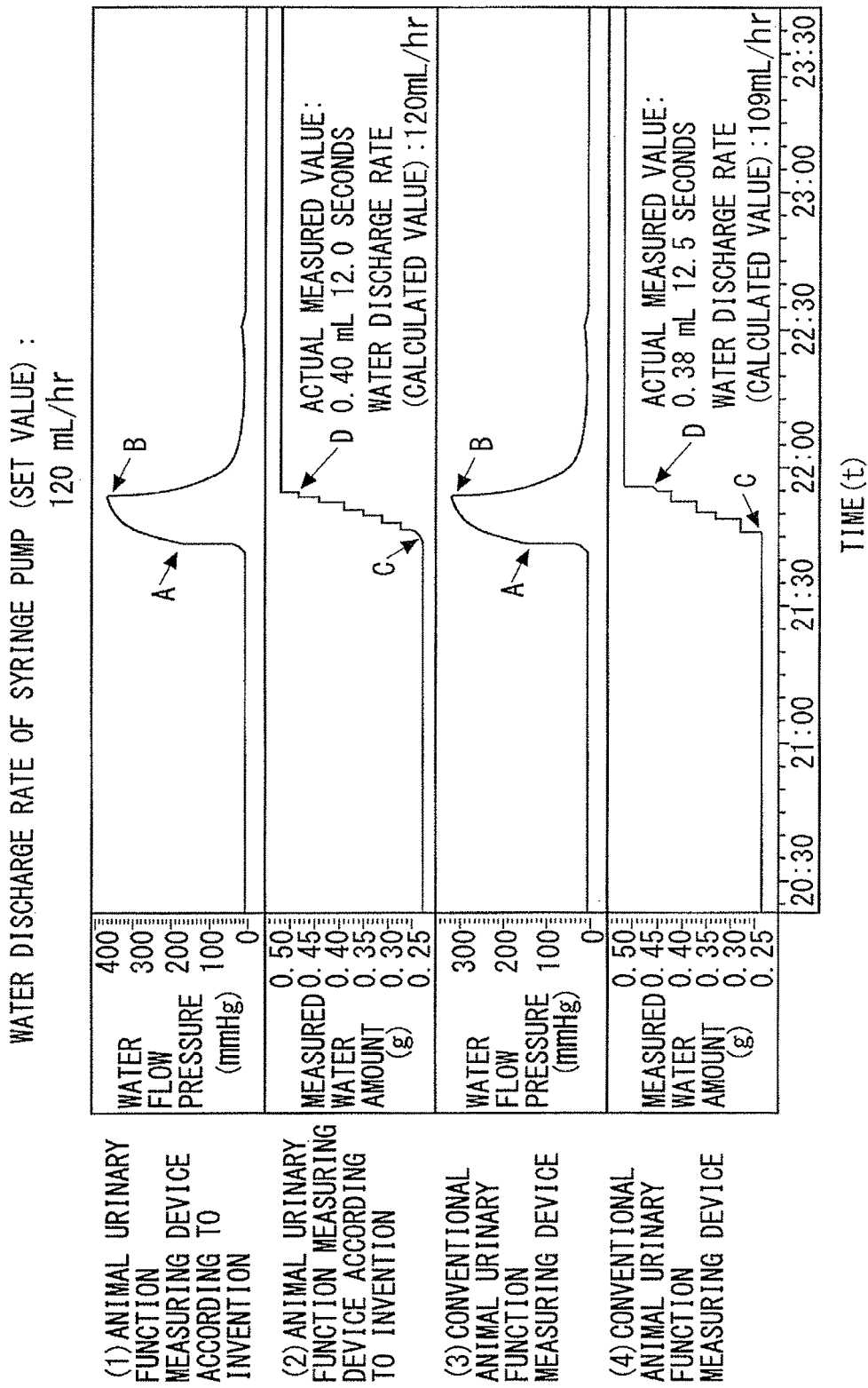

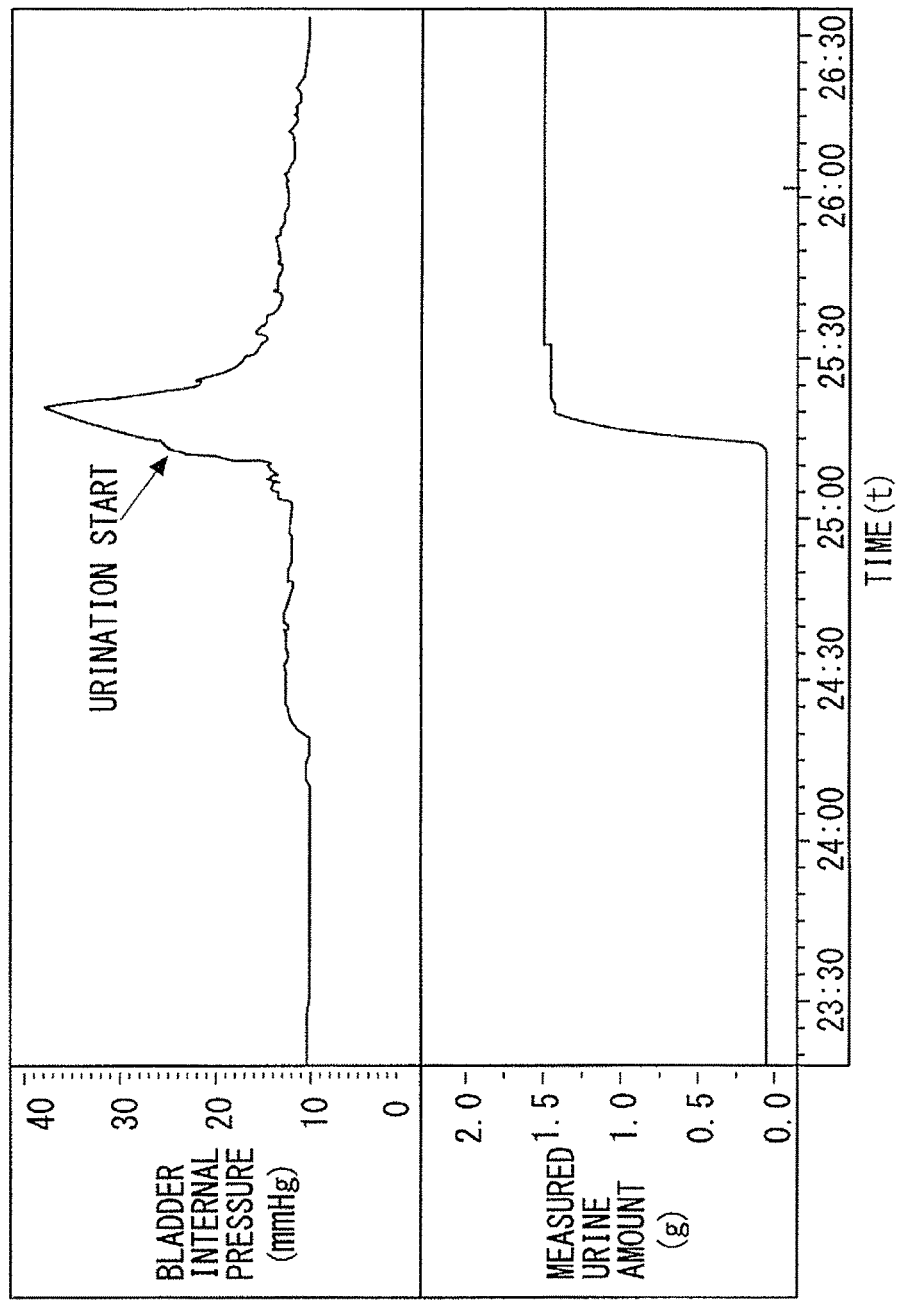

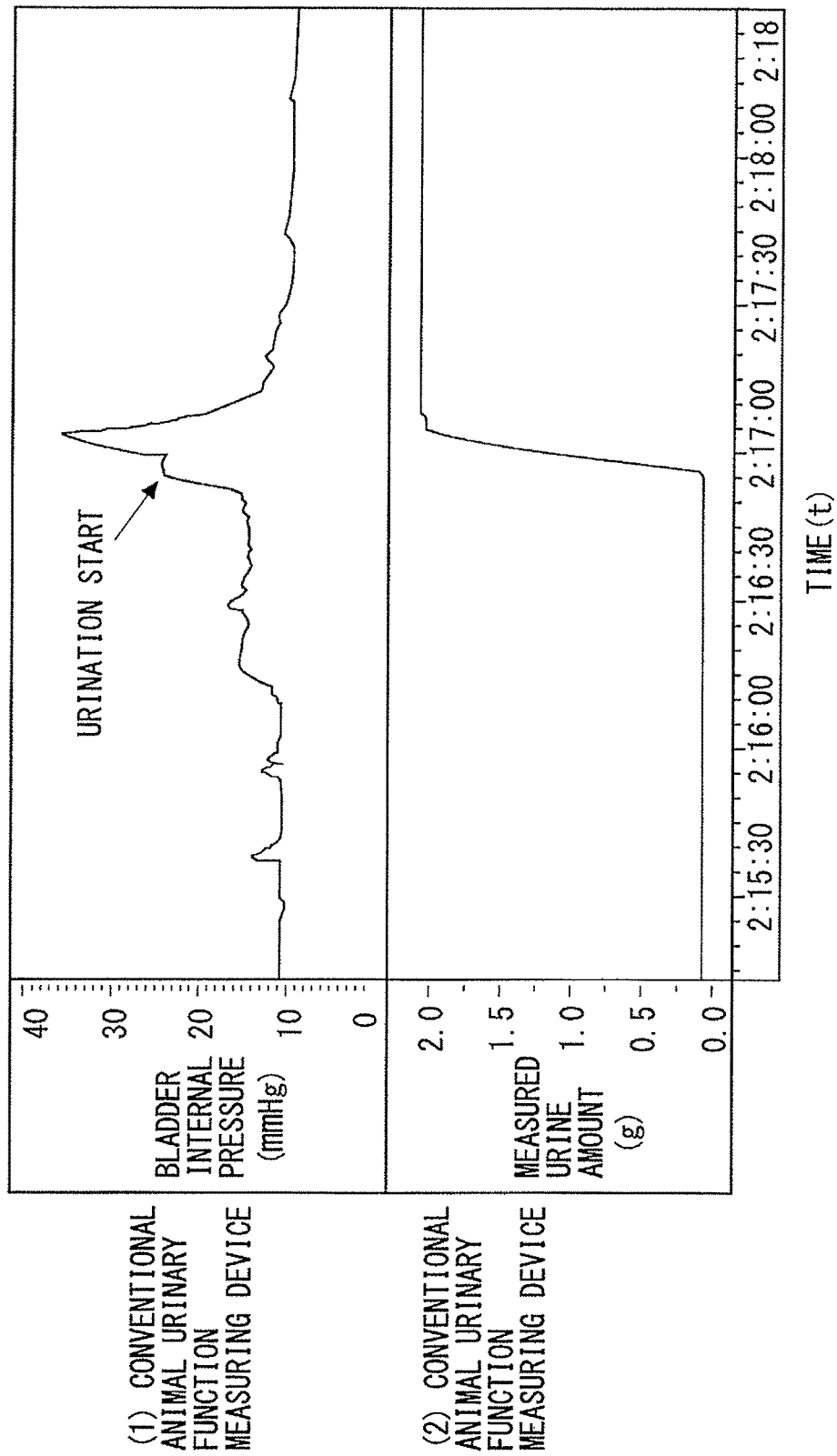

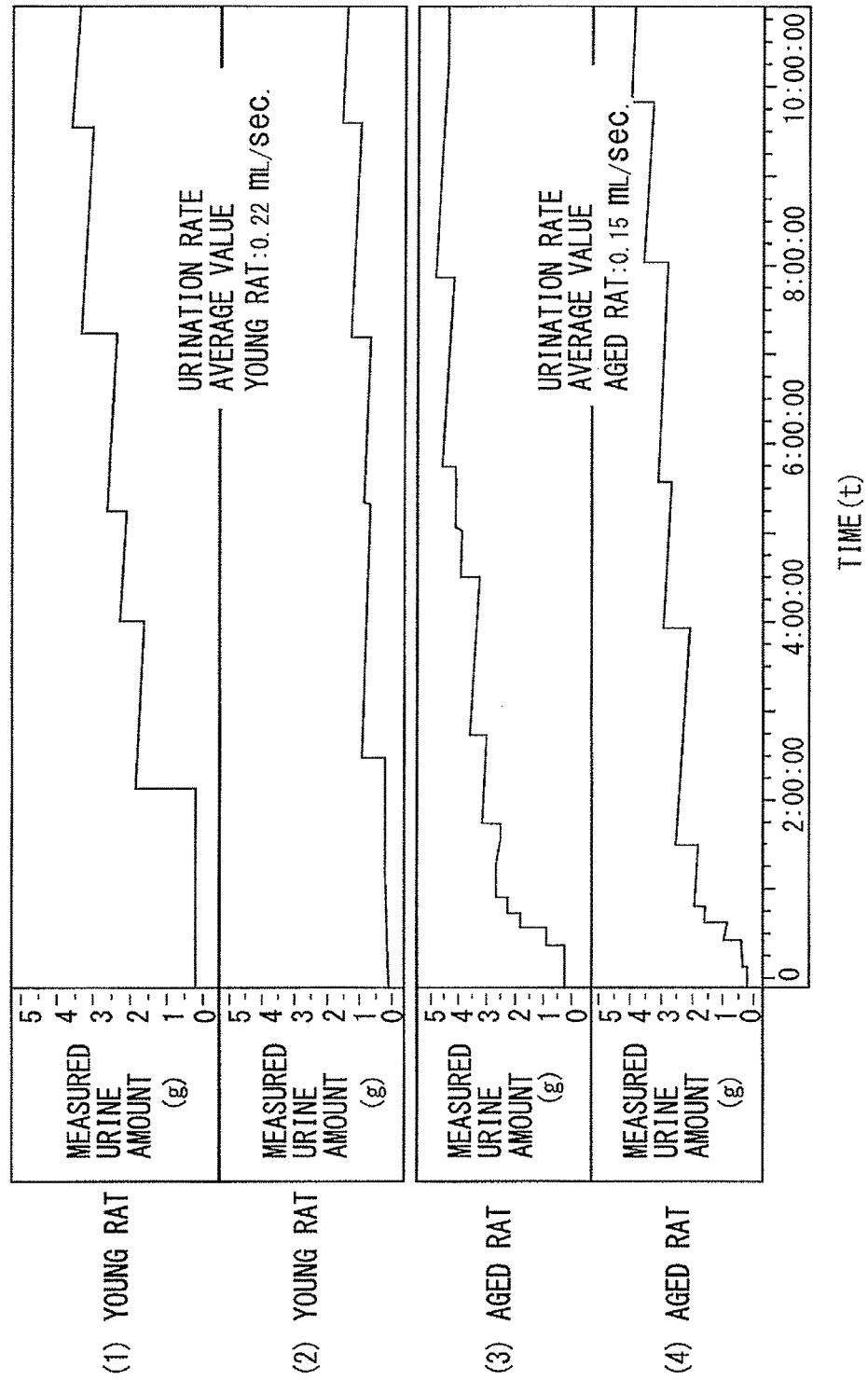

ANIMAL URINARY FUNCTION MEASURING DEVICE AND ANIMAL URINARY FUNCTION MEASURING METHOD

FIELD

The present invention relates to an animal urinary function measuring device and an animal urinary function measuring method which measure urinary functions such as a urine amount and a urination rate of an animal.

BACKGROUND

In pharmacological studies in the urological field, the urine amount and the number of urinations of an animal are measured and the measured data is used as an indicator for examining the health condition of the animal and an effect of a medication. In addition, in order to examine the health condition of the animal and the effect of the medication in detail, the measurement of a urination rate and the use of the urination rate as the indicator are in demand. Although the measurement of the urine amount of the animal has been carried out conventionally by, e.g., visually checking a change in urine amount collected in a measuring cylinder at predetermined time intervals, the conventional measurement has had a problem that the conventional measurement requires a large amount of labor.

In order to solve the above-described problem, there is developed an automatic urine measuring device for a small animal using an electronic balance which has the purpose of automatically removing noises and further automatically determining the urine amount (see Patent Document 1). In addition, there are developed a water drinking amount/urine amount automatic measuring device for an animal and a system using the device which automatically measure the water drinking amount and the urine amount continuously and simultaneously to allow the acquisition of time-sequential data collectively indicative of the water drinking amount and the urine amount and automatic outputting of the detailed data only when an animal drinks water or urinates (see Patent Document 2).

[Patent Document 1] Japanese Patent Application Laid-open No. 2002-365283
[Patent Document 2] Japanese Patent Application Laid-open No. 2006-226919

SUMMARY

However, in the conventional measurement of the urine amount of the animal, the urine of the animal adheres to a wall or a net, and hence the accuracy in the sampling of the urine has been low and it has not been possible to time-sequentially measure the urine amount with accuracy. In addition, according to differences in urine amount and the viscosity of the urine, time required for the urine to reach the balance through a funnel differs. As a result, the urination rate cannot be measured so that there has been a problem in the assessment of the health condition of the animal and the effect of a medication which requires accuracy.

In view of the above-described problems, an object of the present invention is to provide an animal urinary function measuring device and an animal urinary function measuring method each with high accuracy in the sampling of the urine amount of the animal.

In order to solve the above-described problems, the present invention has devised the provision of a reticulated portion as a fine net between an accommodating portion and a collecting portion. With this arrangement, it is possible to provide the animal urinary function measuring device and the animal urinary function measuring method each with high accuracy in the sampling of the urine amount of the animal.

Specifically, an animal urinary function measuring device according to the present invention includes: an accommodating portion which accommodates an animal other than a human; a collecting portion which is provided below the accommodating portion and collects urine discharged by the animal in the accommodating portion; a reticulated portion which is provided between the accommodating portion and the collecting portion, allows passage of the urine of the animal into the collecting portion, collects an object other than the urine, and whose wire diameter of a net thereof being not more than 0.5 mm and whose mesh size being not less than 1 $mm^2$ and not more than a maximum mesh size determined by at least one of excrement of the animal accommodated in the accommodating portion and a predetermined object used to accommodate the animal in the accommodating portion; a measuring portion which measure a weight of the urine collected by the collecting portion; and a data recording portion which records data measured by the measuring portion.

The animal accommodated in the accommodating portion urinates and defecates in the accommodating portion. The reticulated portion is provided between the accommodating portion and the collecting portion, allows the passage of the urine of the animal into the collecting portion, and collects the object other than the urine. The wire diameter of the net of the reticulated portion is not more than 0.5 mm, and it is thereby possible to prevent the adhesion of the urine to the reticulated portion. In addition, the mesh size of the reticulated portion is not less than 1 $mm^2$, it is thereby possible to prevent a situation where the urine cannot pass through the reticulated portion due to the influence of surface tension or the like. The mesh size of the reticulated portion is not more than the maximum mesh size determined by at least one of the excrement of the animal accommodated in the accommodating portion and the predetermined object used to accommodate the animal in the accommodating portion. Note that the predetermined object used to accommodate the animal in the accommodating portion is food or the like. Consequently, since the reticulated portion allows the passage of the urine and collects the object other than the urine, it is possible to reliably separate the urine from the object other than the urine. The urine having passed through the reticulated portion is allowed to enter into the collecting portion, and the measuring portion can accurately measure the weight of the urine collected by the collecting portion. Further, the data recording portion records the data measured by the measuring portion. With the arrangement described above, the animal urinary function measuring device according to the present invention is capable of enhancing the accuracy in the sampling of the urine amount of the animal to accurately measure the urine amount time-sequentially, and accurately detect the symptoms of the animal such as pollakiuria, polyuria, oliguria, or dysuria.

In addition, in the animal urinary function measuring device according to the present invention, the reticulated portion may be provided as a bottom surface of the accommodating portion. As a result, it is possible to reduce the size of the animal urinary function measuring device according to the present invention.

Further, the animal urinary function measuring device according to the present invention may further include a funneling portion which is provided between the reticulated portion and the collecting portion, has a shape having an open upper part and a narrow lower part that is in contact with the collecting portion, and funnels the urine discharged by the animal in the accommodating portion into the collecting portion.

The funneling portion has the shape having the open upper part and the narrow lower part, whereby the urine does not scatter between the accommodating portion and the collecting portion so that the collecting portion can reliably collect the urine. As a result, the measuring portion can accurately measure the weight of the urine collected by the collecting portion. In addition, the lower part of the funneling portion is in contact with the collecting portion, the measuring portion can thereby measure the weight of the urine at a time point when the urine adheres to the funneling portion. Consequently, the animal urinary function measuring device according to the present invention is capable of measuring the accurate urine amount on a real-time basis.

Furthermore, the animal urinary function measuring device according to the present invention may further include a reticulated portion attaching/detaching portion which is provided below the accommodating portion and is capable of attaching and detaching the reticulated portion. The animal urinary function measuring device according to the present invention includes the reticulated portion attaching/detaching portion, whereby, when the mesh of the reticulated portion is clogged with feces or the like, or when the measurement is started with a new animal, it is possible to easily replace the reticulated portion with a new one.

Herein, the animal urinary function measuring device according to the present invention may further include a urination rate calculating portion which calculates a rate of urination based on the data recorded by the data recording portion. The animal urinary function measuring device according to the present invention has high accuracy in the sampling of the urine amount of the animal, and hence the urination rate calculating portion can accurately calculate the urination rate. As a result, the animal urinary function measuring device according to the present invention is capable of more accurately examining the health condition of the animal and the effect of a medication.

Moreover, the animal urinary function measuring device according to the present invention may further include a second accommodating portion which has a size matching an activity area of the animal in the accommodating portion. The animal urinary function measuring device according to the present invention includes the second accommodating portion which has the size matching the activity area of the animal, it is thereby possible to measure urinary functions of a plurality of species of the animals in one accommodating portion.

In addition, in the animal urinary function measuring device according to the present invention, the reticulated portion is preferably provided obliquely relative to the bottom surface of the accommodating portion. By installing the reticulated portion obliquely, it is possible to gather objects other than the urine such as feces and food in a lower part where the urine does not pass. That is, the objects other than the urine such as the feces and the food which have dropped from the above come in contact with the obliquely installed reticulated portion and the dropping direction is thereby changed, and hence it becomes possible to separate the urine from the feces and the food. As a result, it is possible to prevent a situation where the urine hits the feces or the food to disappear and the accurate measurement of the urine is thereby hindered.

Further, the present invention can be defined as an animal urinary function measuring method for measuring the urinary function of the animal by using the above-described animal urinary function measuring devices.

According to the present invention, it becomes possible to provide the animal urinary function measuring device and the animal urinary function measuring method each with high accuracy in the sampling of the urine amount of the animal.

BRIEF DESCRIPTION OF THE DRAWINGS

FIG. 7 is a graph showing the relationship between a water flow pressure and time and the relationship between a water amount and time in an animal urinary function measuring device according to Embodiment 1 of the present invention;

FIG. 8 is a graph showing the relationship between the internal pressure of a bladder and time in cystometry measurement using an animal urinary function measuring device according to Embodiment 2 of the present invention;

FIG. 9 is a graph showing the relationship between the internal pressure of the bladder and time in the cystometry measurement using the conventional animal urinary function measuring device;

FIG. 10 is a graph showing the relationship between a measured urine amount and time when young rats and aged rats are used in an animal urinary function measuring device according to Embodiment 3 of the present invention;

DESCRIPTION OF EMBODIMENTS

A description is given of an animal urinary function measuring device 1 according to an embodiment of the present invention with reference to the drawings. The embodiment shown below is shown by way of example only, and the present invention is not limited thereto. The urinary function which the animal urinary function measuring device 1 according to the embodiment of the present invention can measure is not limited as long as it is obtained from a urine amount and a urination rate, and examples thereof include pollakiuria, polyuria, oliguria, and dysuria.

Figure 1:
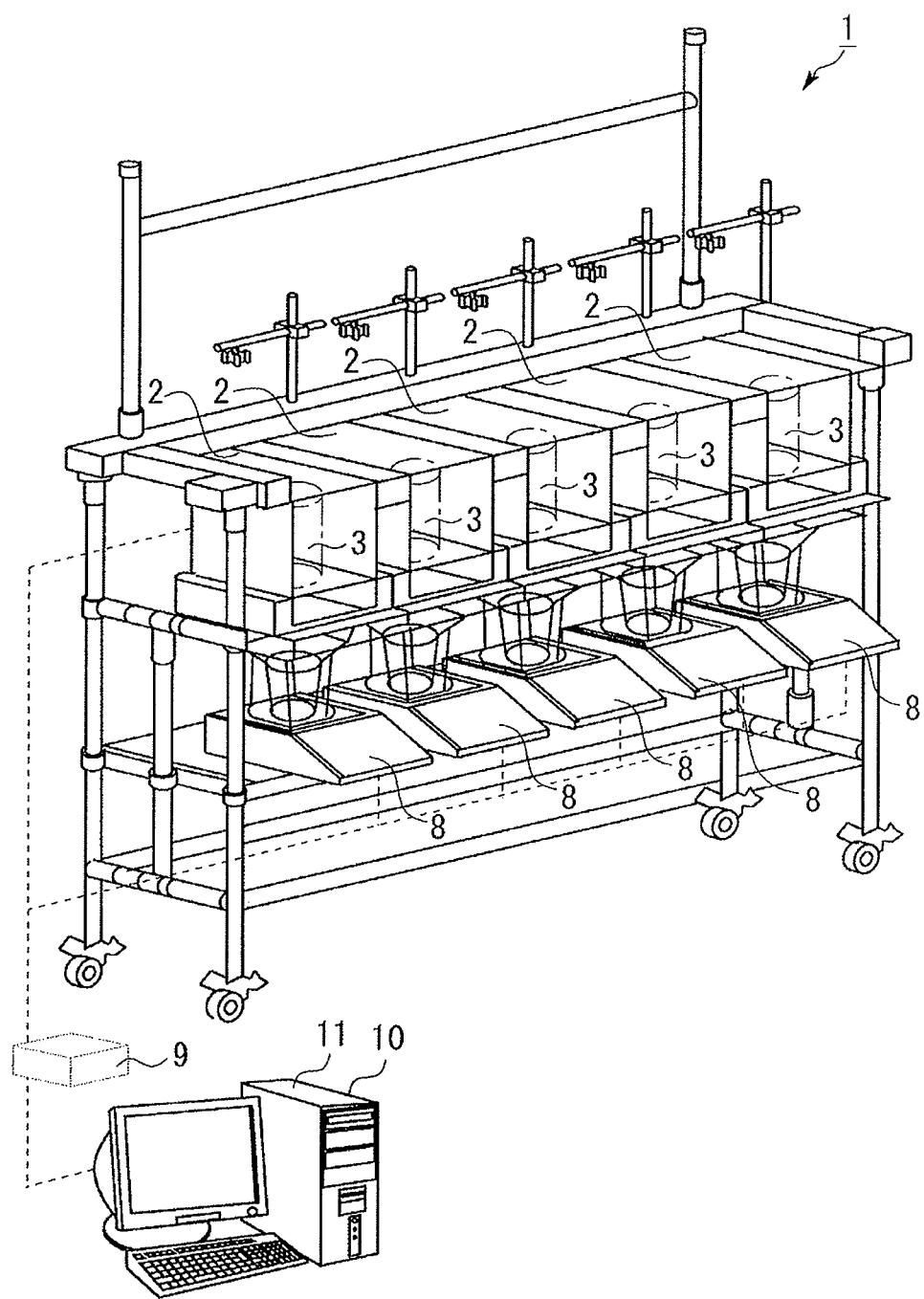
FIG. 1 is a perspective view when a plurality of animal urinary function measuring devices according to an embodiment of the present invention are provided.
Figure 2A:
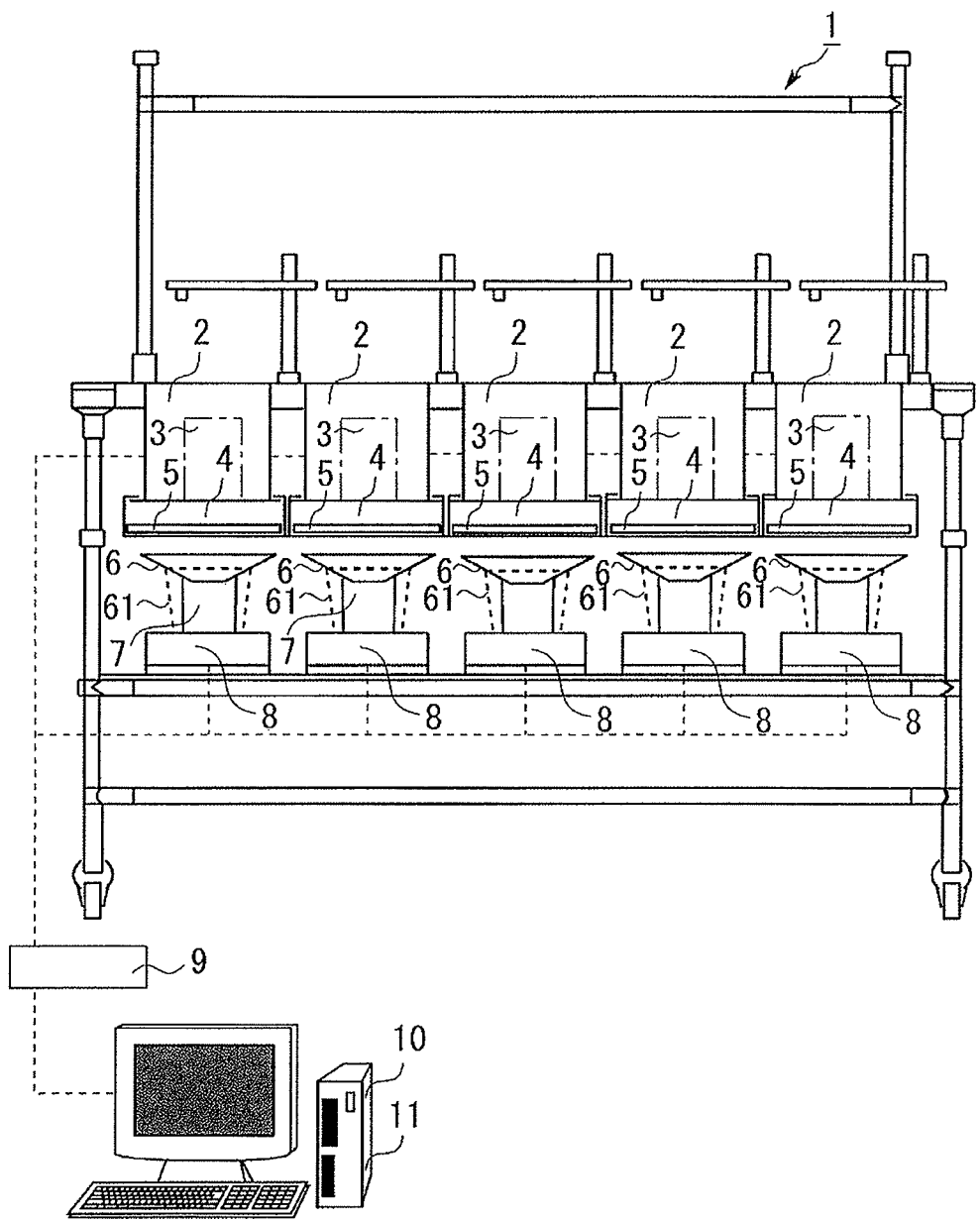
FIG. 2A is a front view when a plurality of the animal urinary function measuring devices according to the embodiment of the present invention are provided.
Figure 2B:
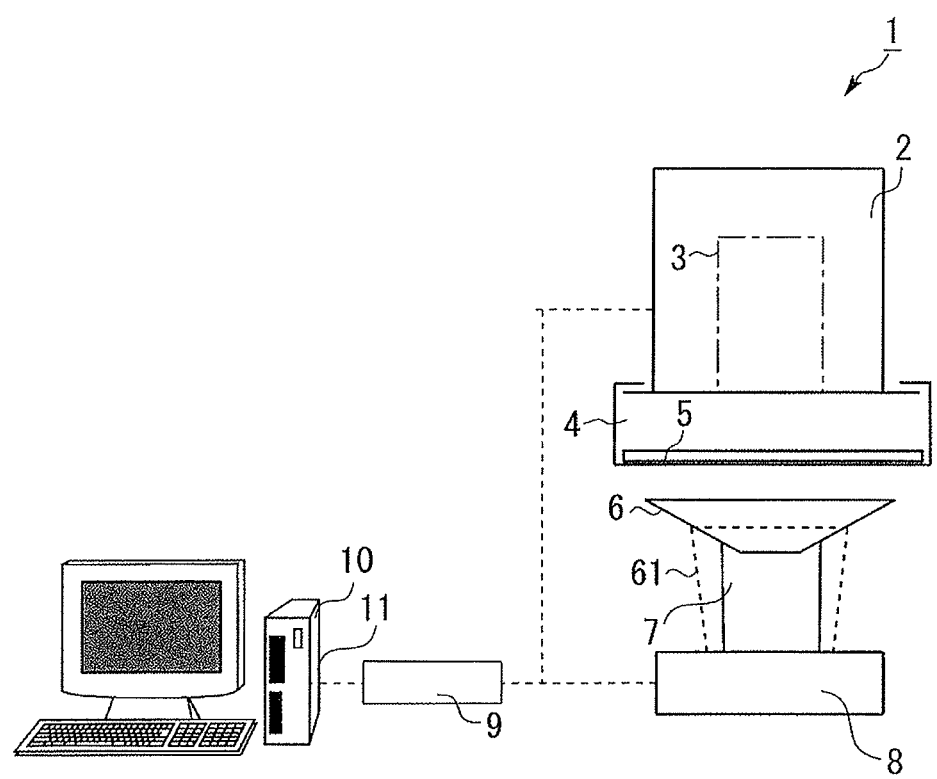
FIG. 2B is a front view of the animal urinary function measuring device according to the embodiment of the present invention.

A description is given of the individual components of the animal urinary function measuring device 1 according to the embodiment of the present invention. As shown in FIGS. 1, 2A, and 2B, the animal urinary function measuring device 1 according to the embodiment of the present invention mainly includes an accommodating portion 2 (cage), a second accommodating portion 3, a reticulated portion attaching/detaching portion 4, a reticulated portion 5, a funneling portion 6, a collecting portion 7, a measuring portion 8, a data recording portion 9, and a urination rate calculating portion 10. Hereinbelow, a specific description is given of each component. As shown in FIGS. 1 and 2A, when a plurality of the animal urinary function measuring devices 1 according to the embodiment of the present invention are provided, although there are cases where the animal urinary function measuring devices 1 are installed on a movable pipe rack, the place of the installation is not particularly limited.

Figure 4A:
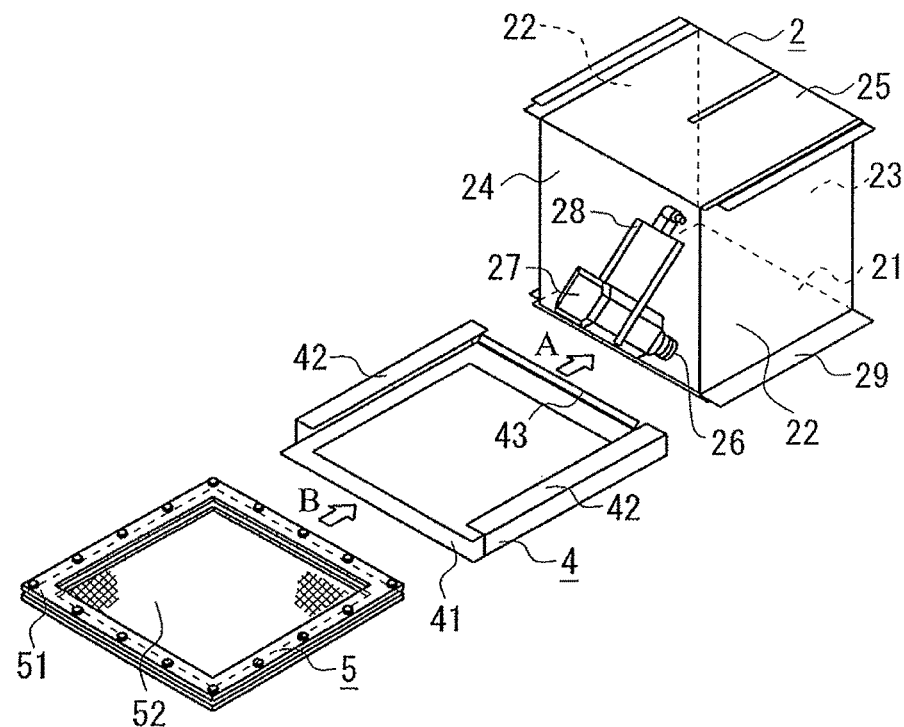
FIG. 4A is a schematic diagram showing a state where a reticulated portion is being installed in the accommodating portion in the animal urinary function measuring device according to the embodiment of the present invention.

First, the accommodating portion 2 is described. The accommodating portion 2 accommodates animals other than humans. The animals other than humans are not particularly limited as long as they can be raised and observed in the accommodating portion 2, and examples of the animals include monkeys, dogs, rabbits, rats, guinea pigs, hamsters, and mice. In addition, as shown in FIG. 4A, the accommodating portion 2 is in the shape of a substantially cubic box, and has a bottom surface 21 formed of a fluorine-coated metal net, an upper surface 25 formed of a transparent plate made of polyvinyl chloride, and side surfaces 22, a front surface 23, and a rear surface 24 formed of stainless plates. The upper surface 25 is formed of the transparent plate, and a measurer can thereby easily observe the state in the accommodating portion 2. In addition, the metal net of the bottom surface 21 is coated with fluorine, whereby urine discharged by an animal accommodated in the accommodating portion 2 is less likely to adhere to the metal net, and the urine is passed to the reticulated portion 5. The mesh of the bottom surface 21 desirably has the size which allows the excrement of the animal or the like to pass through the mesh. In the animal urinary function measuring device 1 according to the embodiment of the present invention, although the wire diameter of the metal net of the bottom surface 21 of the accommodating portion 2 is 1.5 mm and the mesh size is 15 mm$^2$, they are not limited to these sizes, and the accommodating portion 2 is not limited to the above-described materials. The material may be appropriately selected in accordance with the species of the animal to be accommodated and, in the case of relatively large animals such as monkeys and dogs, a metal cage is suitable.

Figure 4B:
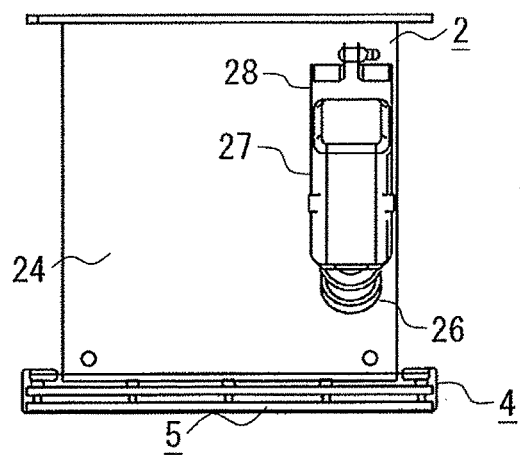
FIG. 4B is a rear view showing the state where the reticulated portion is installed in the accommodating portion in the animal urinary function device according to the embodiment of the present invention.
Figure 4C:
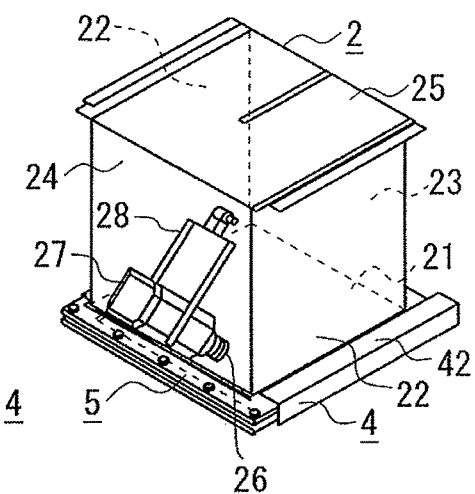
FIG. 4C is a perspective view showing the state where the reticulated portion is installed in the accommodating portion in the animal urinary function device according to the embodiment of the present invention.

Further, in the rear surface 24 of the accommodating portion 2, as shown in FIGS. 4A to 4C, there is provided a water supply opening 26 such that the animal accommodated in the accommodating portion 2 can be supplied with water, and a water supply bottle 27 is manually attached to the water supply opening 26 from the outside of the accommodating portion 2. Furthermore, a water supply bottle holder 28 on which the water supply bottle 27 can be hung is attached above the water supply opening 26. Moreover, as shown in FIG. 4A, to the lower ends of the side surfaces 22 of the accommodating portion 2, in order to attach the reticulated portion attaching/detaching portion 4 to the accommodating portion 2, a tongue portion 29 is attached along the lower sides of the side surfaces 22 in a direction perpendicular to and outward from the side surfaces 22. In addition, in the animal urinary function measuring device 1 according to the embodiment of the present invention, in a case where cystometry measurement as measurement of the internal pressure of an urethra of a bladder resulting from the injection of water is concurrently conducted, a pressure transducer (not shown) and a pressure amplifier (not shown) are provided in the accommodating portion 2 in order to measure the bladder pressure of the animal.

Figure 3A:
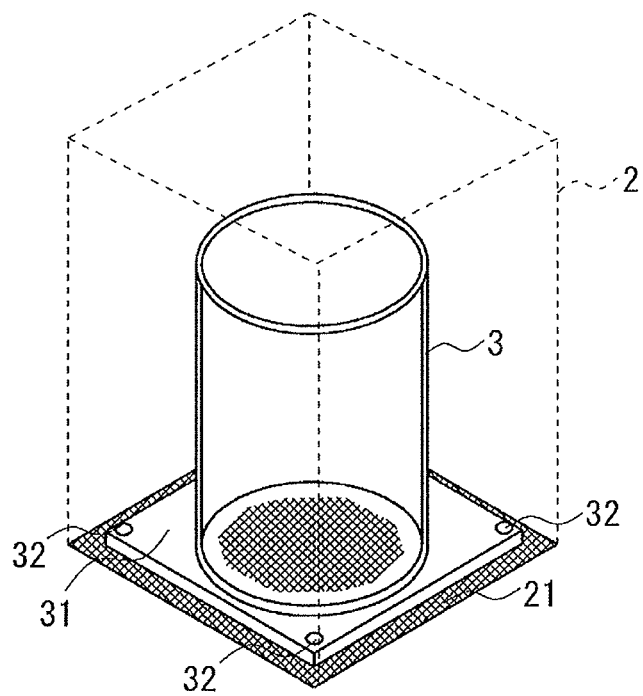
FIG. 3A is a perspective view showing the inside of an accommodating portion in the animal urinary function measuring device according to the embodiment of the present invention.
Figure 3B:
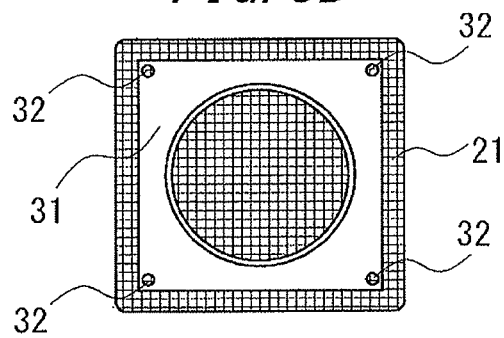
FIG. 3B is a top view showing the inside of the accommodating portion in the animal urinary function measuring device according to the embodiment of the present invention.
Figure 3C:
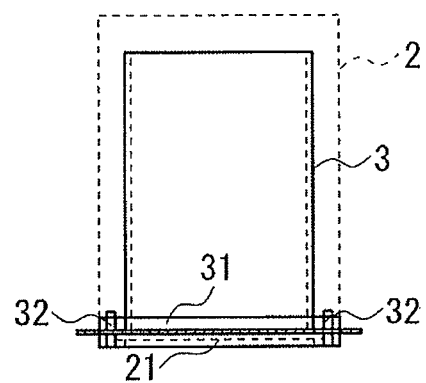
FIG. 3C is a side view showing the inside of the accommodating portion in the animal urinary function measuring device according to the embodiment of the present invention.

The second accommodating portion 3 is described. The second accommodating portion 3 is provided in the accommodating portion 2 and, as shown in FIGS. 3A to 3C, the second accommodating portion 3 is a cylindrical tube having a size matching the activity area of the animal. On the metal net provided in the bottom surface 21 of the accommodating portion 2, a plate portion 31 from which a part thereof corresponding to the area of the bottom surface of the second accommodating portion 3 is removed is fixed by using screws 32. The second accommodating portion 3 is fitted in the removed part of the plate portion 31, whereby the second accommodating portion 3 is attached to the accommodating portion 2. For example, when the measurement is conducted by using a mouse in the accommodating portion 2 capable of raising a rat, as shown in FIG. 3A, the second accommodating portion 3 having the size matching the activity area of the mouse can be installed in the accommodating portion 2 and used. As long as the animal can be accommodated in the accommodating portion 2, only by changing the size of the second accommodating portion 3, it becomes possible to conduct measurement using a plurality of species of animals in one accommodating portion 2. The shape and the material of the second accommodating portion 3 may be any shape and material as long as the action of the animal is not affected, and the material thereof is preferably transparent such that the action of the animal can be observed.

The reticulated portion attaching/detaching portion 4 and the reticulated portion 5 are described. As shown in FIG. 4A, the reticulated portion attaching/detaching portion 4 has a frame portion 41 having substantially the same length as that of the side of the bottom surface 21 of the accommodating portion. 2, hook portions 42 which are provided along sides of the frame portion 41 corresponding to side-surface sides of the accommodating portion 2 and are upwardly formed into an inverted L shape, and a stopper portion 43 which is provided along the side of the frame portion 41 corresponding to the front surface side of the accommodating portion 2 and is upwardly formed, and a hollow is formed in the center of the reticulated portion attaching/detaching portion 4. The hook portions 42 are hooked on the tongue portion 29 of the accommodating portion 2 and are slid from the rear side of the accommodating portion 2 (a direction indicated by an arrow A of FIG. 4A) along the bottom surface 21 of the accommodating portion 2, whereby the reticulated portion attaching/detaching portion 4 is attached to the accommodating portion 2 such that the frame portion 41 and the bottom surface 21 of the accommodating portion 2 oppose each other. Note that the reticulated portion attaching/detaching portion 4 may also be attached to the accommodating portion 2 by being slid from the front side of the accommodating portion 2 (a direction opposite to the direction indicated by the arrow A of FIG. 4A) along the bottom surface 21 of the accommodating portion 2.

As shown in FIGS. 4A and 5A to 5C, the reticulated portion 5 has a fine net frame portion 51 having a shape substantially identical with that of the frame portion 41 of the reticulated portion attaching/detaching portion 4 and a fine net portion 52 as a fine net which is formed so as to cover a central hollow formed by the fine net frame portion 51. The reticulated portion 5 is passed between the hook portions 42 and 42 from the frame portion 41 on the side opposing the frame portion 41 on the side where the stopper portion 43 of the reticulated portion attaching/detaching portion 4 is provided (a direction indicated by an arrow B of FIG. 4A), and slides on the frame portion 41. The reticulated portion 5 abuts on the stopper portion 43 of the reticulated portion attaching/detaching portion 4, whereby the sliding thereof is stopped, and the reticulated portion 5 is attached to the reticulated portion attaching/detaching portion 4. As shown in FIGS. 4B and 4C, the reticulated portion attaching/detaching portion 4 having the reticulated portion 5 attached thereto is attached to the accommodating portion 2, whereby the reticulated portion 5 is also attached to the accommodating portion 2. The reticulated portion 5 may also be provided as the bottom surface 21 of the accommodating portion 2 (not shown), or the reticulated portion attaching/detaching portion 4 may be provided above the bottom surface 21 of the accommodating portion 2 and the reticulated portion 5 may be attached above the bottom surface 21 of the accommodating portion 2 (not shown). Note that, by making the reticulated portion 5 movable, when the fine net portion 52 is clogged with crud or the like, it is possible to efficiently renew the reticulated portion 5, and convenience is thereby enhanced. In addition, as shown in FIGS. 4A to 4C, in the case where the reticulated portion 5 is attached below the bottom surface 21 of the accommodating portion 2, the bottom surface 21 of the accommodating portion 2 collects objects larger than the size of the mesh of the metal net, and the reticulated portion 5 allows the passage of the urine and collects objects other than the urine, and hence the separation of the urine from the objects other than the urine is efficient and the frequency of replacement of the reticulated portion 5 is reduced as compared with a case where the reticulated portion 5 is incorporated as the bottom surface 21 of the accommodating portion 2.

The fine net portion 52 of the reticulated portion 5 is described. The fine net portion 52 is a fine net which allows the passage of the urine of the animal into the funneling portion 6 and collects objects other than the urine. Although the mesh configuration of the fine net portion 52 may have any configuration, the mesh size of the reticulated portion 5 is not more than the maximum mesh size determined by at least one of the excrement of the animal accommodated in the accommodating portion 2 and a predetermined object used to accommodate the animal in the accommodating portion 2. Note that the predetermined object used to accommodate the animal in the accommodating portion 2 is food or the like. For example, the mesh size is preferably about 2 $mm^2$ or less for mice, about 5 $mm^2$ or less for rats, guinea pigs, and hamsters, and about 10 $mm^2$ or less for rabbits. The mesh size of the reticulated portion 5 can be appropriately changed in accordance with a target animal, and the mesh size thereof for an animal smaller than the target animal can be used. In addition, when the mesh of the reticulated portion 5 is extremely fine, water cannot pass therethrough due to the influence of surface tension or the like, and hence the mesh size is preferably about 1 $mm^2$ or more.

Further, the wire diameter of the fine net portion 52 is extremely smaller than that of a conventional metal net, and is 0.5 mm or less, preferably 0.2 mm or less, more preferably 0.1 mm or less, further preferably 0.06 mm or less, and further more preferably 0.03 mm or less. The material constituting the fine net portion 52 of the reticulated portion 5 may be any material as long as it is strong enough to resist the action of the animal and periodic cleaning, and is rendered water-repellent so as not to absorb water. Specific examples of the material include metal, nylon, polyethylene, and fluorocarbon, and water-repellent metal is especially preferable.

Figure 5A:
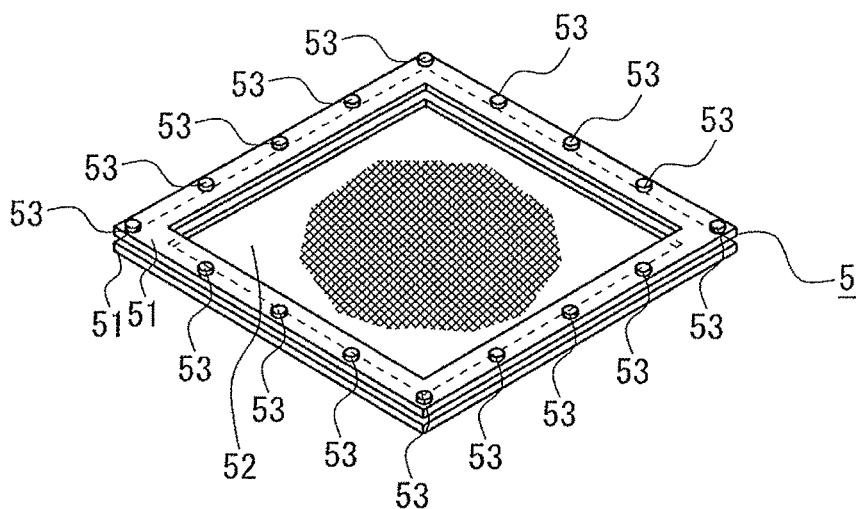
FIG. 5A is a perspective view showing the reticulated portion in the animal urinary function measuring device according to the embodiment of the present invention.
Figure 5B:
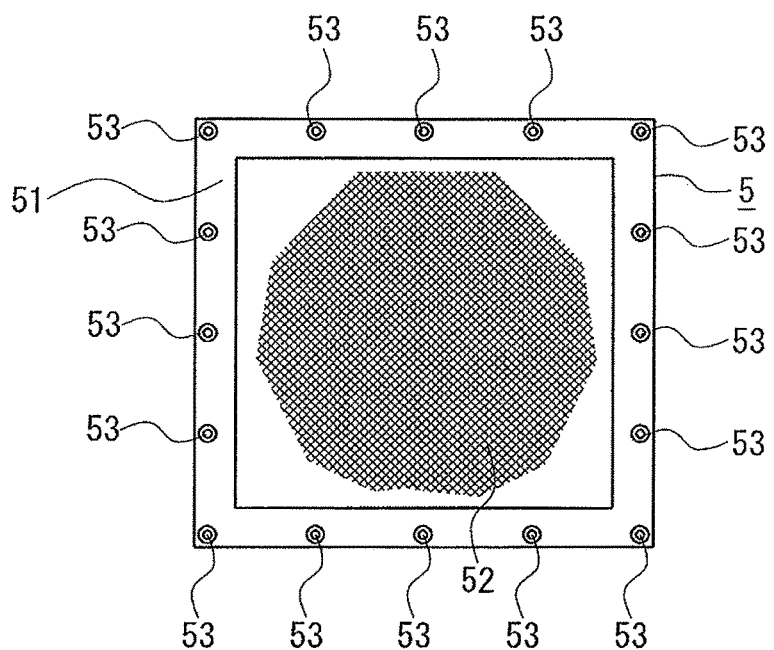
FIG. 5B is a top view showing the reticulated portion in the animal urinary function measuring device according to the embodiment of the present invention.
Figure 5C:
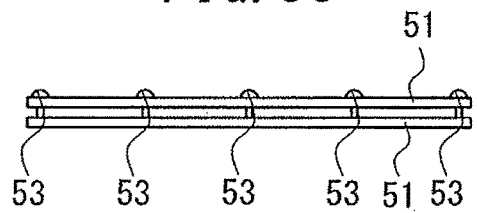
FIG. 5C is a side view showing the reticulated portion in the animal urinary function measuring device according to the embodiment of the present invention.

As a method for producing the fine net portion 52 of the reticulated portion 5, it is possible to produce the fine net portion 52 by braiding a line made of the above-described material into a lattice shape. When specifically describing the method for producing the fine net portion 52 having the mesh size of about 1 $mm^2$, the fine net frame portion 51 is a metal frame of 230 mm×200 mm, and is provided with grooves at the pitch of 2 mm. Subsequently, a metal line having a diameter of 0.06 mm (a composite metal line for sweetfish fishing (e.g.; manufactured by MORRIS. CO, LTD)) is wound around the fine net frame portion 51 in longitudinal and lateral directions while being hooked in the grooves, whereby the fine net portion 52 is produced. The mesh size of the fine net portion 52 is about 2 $mm^2$. Two fine net frame portions 51 each formed with the fine net portion 52 are prepared and, as shown in FIGS. 5A to 5C, the two fine net frame portions 51 are stacked on each other and fixed to each other using screws 53. As a result, the reticulated portion 5 has a two-stage structure, and the mesh size of the fine net portion 52 is about 1 $mm^2$ when the reticulated portion 5 is viewed from immediately above. The reticulated portion 5 having the two fine net frame portions 51 stacked on each other is attached to the reticulated portion attaching/detaching portion 4. Note that the reticulated portion 5 may have one fine net frame portion 51 instead of the two fine net frame portions 51 stacked on each other. In this case, in the reticulated portion 5, the fine net frame portion 51 is provided with the grooves at the pitch of 1 mm such that the mesh size of the fine net portion 52 becomes about 1 mm². Subsequently, the fine net portion 52 may be produced by hooking the metal line in the grooves.

The funneling portion 6 is described. As shown in FIGS. 1, 2A, and 213, the funneling portion 6 is provided between the reticulated portion 5 and the collecting portion 7, is in a funnel-like shape having a widely opened inlet on the reticulated portion 5 side (corresponding to an upper part of a funneling portion of the present invention) and a narrow outlet on the collecting portion 7 side (corresponding to a lower part of the funneling portion of the present invention), and funnels the urine discharged by the animal in the accommodating portion 2 into the collecting portion 7 via the reticulated portion 5. As a result, the urine does not scatter between the accommodating portion 2 and the collecting portion 7 so that the collecting portion 7 can reliably collect the urine. Consequently, in the animal urinary function measuring device 1 according to the embodiment of the present invention, the measuring portion 8 can accurately measure the weight of the urine collected by the collecting portion 7. In addition, the outlet of the funneling portion 6 on the collecting portion 7 side is provided in contact with the collecting portion 7. As a result, at a time point when the urine adheres to the funneling portion 6, the measuring portion 8 can measure the weight of the urine. Accordingly, in the animal urinary function measuring device 1 according to the embodiment of the present invention, the measuring portion 8 can measure the accurate urine on a real-time basis. The funneling portion 6 is held above the measuring portion 8 by a funneling portion holding portion 61 indicated by dotted lines in FIGS. 2A and 2B. The funneling portion holding portion 61 is provided above the measuring portion 8, supports the funneling portion 6 from below, and is formed of a wire.

The collecting portion 7 is described. As shown in FIGS. 1, 2A, and 2B, the collecting portion 7 is a cup-like vessel, and an opening of the collecting portion 7 has a diameter larger than that of the outlet of the funneling portion 6 on the collecting portion 7 side. In addition, the upper part of the collecting portion 7 is provided in contact with the outlet of the funneling portion 6 on the collecting portion 7 side, and the bottom surface of the collecting portion 7 is provided in contact with the measuring portion 8. The collecting portion 7 collects the urine discharged by the animal in the accommodating portion 2 via the reticulated portion 5 and the funneling portion 6. The urine collected in the collecting portion 7 can be used in analysis of a clinical test and a biochemical test.

The measuring portion 8 is described. The measuring portion 8 may be any balance as long as it can measure the weight of the urine, and a precision balance with a precision of 0.01 g or more is preferable. In addition, the measuring portion 8 preferably includes the function of externally outputting measured data. On the measuring portion 8, the collecting portion 7, the funneling portion 6, and the funneling portion holding portion 61 are placed. Accordingly, the measuring portion 8 can measure the weight of the urine collected by the collecting portion 7 and the weight of the urine adhered to the funneling portion 6. As a result, the measuring portion 8 can measure the weight at a time point when the urine having passed through the reticulated portion 5 is received by either the funneling portion 6 or the collecting portion 7, and hence there is no time lag.

The data recording portion 9 is described. As the data recording portion 9, Power Lab (manufactured by AD INSTRUMENTS) is used and, as shown in FIGS. 1, 2A, and 2B, the data recording portion 9 is bus-connected to at least the measuring portion 8, the pressure transducer (not shown) and the pressure amplifier (not shown) which are provided in the accommodating portion 2. The data recording portion 9 records data measured in the measuring portion 8, the pressure transducer (not shown), and the pressure amplifier (not shown). In addition, the data recording portion 9 converts electronic signals obtained from the measuring portion 8, the pressure transducer (not shown), and the pressure amplifier (not shown) to analog signals, and transmits the analog signals to a computer 11. Note that the data may be analog-converted data or digital-converted data. Further, the data recording portion 9 may be any device as long as it can record the data measured in the measuring portion 8, the pressure transducer (not shown), and the pressure amplifier (not shown), and is not limited to Power Lab.

Furthermore, the data recording portion 9 records data to be recorded as a urination start time, a urination termination time, and a measured urine weight value at a predetermined time interval (e.g., an interval of 0.25 seconds). For example, although the measured urine weight value may be measured and acquired as a value including the weight of each of the collecting portion 7, the funneling portion 6, and the funneling portion holding portion 61, the real urine weight exclusive of the weight of each of the collecting portion 7, the funneling portion 6, and the funneling portion holding portion 61 may be preferably acquired directly as the measured value. As for the urination start time and the urination termination time, on the basis of the data obtained by the measuring portion 8, a time point when the urine weight starts to rise is set as the urination start time and, after the urine weight has risen once to several times, a time point when no rise in the urine weight is observed within a predetermined time period is set as the urination termination time. Alternatively, in the case of, e.g., a cystometry test, based on the data obtained by the pressure transducer (not shown) and the pressure amplifier (not shown), a time point when the abdominal pressure of the animal starts to rise may be set as the urination start time and, thereafter, a time point when the abdominal pressure of the animal lowers may be set as the urination termination time.

Moreover, the animal urinary function measuring device 1 according to the embodiment of the present invention may include means for processing the data stored by the data recording portion 9 by using the computer 11. As the computer 11, there is used a computer connected to the data recording portion 9 and including various means such as hardware and software required to operate the animal urinary function measuring device 1 according to the embodiment of the present invention in addition to control programs such as an OS (Operating system) and the like, storage means for temporarily storing various data such as an internal memory and the like, input means for inputting an instruction and data to the computer 11 such as a mouse, a keyboard and the like, output means for fetching data processed in the computer 11 such as a monitor, a printer and the like, and various means for causing programs related to the embodiment of the present invention to function. Further, in addition to recording the programs and files related to the embodiment of the present invention in a recording medium such as a CD-ROM or the like and using them by installing them in another computer, the programs and files may be downloaded to another computer by using a distribution server via a network and be used, or only the functions may be utilized. Note that the computer 11 may analyze the analog-converted data by using Lab Chart (manufactured by AD INSTRUMENTS) as an analysis software for Power Lab. Furthermore, the computer 11 may include the urination rate calculating portion 10. The urination rate calculating portion 10 calculates the urination rate based on the data recorded by the data recording portion 9. By calculating the urination rate, it is possible to examine the health condition of the animal and the effect by the medication.

Moreover, in addition to using the animal urinary function measuring device 1 according to the embodiment of the present invention by connecting one computer 11 to one or plurality of combinations of the accommodating portion 2 and the measuring portion 8, the animal urinary function measuring device 1 may also be used by connecting a plurality of the computers 11 to one or a plurality of combinations of the accommodating portion 2 and the measuring portion 8 to construct a network.

With the arrangement described above, according to the animal urinary function measuring device 1 according to the embodiment of the present invention, it becomes possible to provide the animal urinary function measuring device and the animal urinary function measuring method each with high accuracy in the sampling of the urine amount of the animal.

[Embodiment 1]

The urination rate calculated by an animal urinary function measuring device 1 according to Embodiment 1 of the present invention and that calculated by a conventional animal urinary function measuring device 100 are compared and examined. Although the animal urinary function measuring device 1 according to Embodiment 1 of the present invention is the above-described animal urinary function measuring device according to the embodiment of the present invention, the wire diameter of the net of the fine net portion 52 of the reticulated portion 5 is 0.06 mm, and the mesh size thereof is about 1 $mm^2$. In the conventional animal urinary function measuring device 100, the wire diameter of the net of a reticulated portion 50 is 0.5 mm, and the mesh size thereof is about 3 $mm^2$. In addition, in the conventional animal urinary function measuring device 100, a funneling portion 60 is in contact with an accommodating portion 20 and is not contact with a collecting portion 70, and only the collecting portion 70 is placed on a measuring portion 80. As a result, the measuring portion 8 measures only the weight of the urine collected by the collecting portion 7. Other components are similar to those of the above-described animal urinary function measuring device according to the embodiment of the present invention.

An examination method is described. In the accommodating portions 2 of the animal urinary function measuring device 1 according to Embodiment 1 of the present invention and the conventional animal urinary function measuring device 100, polyethylene tubes connected to syringe pumps are placed instead of the animal, and water is simultaneously discharged into the accommodating portions 2 at a flow rate of 120 mL/hr by the pumps while a flow pressure is measured. As the pump, Terufusion Syringe Pump TE-331S, 10 mL Syringe (manufactured by Terumo Corporation) is used.

(1) of FIG. 7 is a graph showing the relationship between a water flow pressure (mmHg) and time (t) in the animal urinary function measuring device 1 according to Embodiment 1 of the present invention. (2) of FIG. 7 is a graph showing the relationship between the measured water amount and time in the animal urinary function measuring device 1 according to Embodiment 1 of the present invention. (3) of FIG. 7 is a graph showing the relationship between the water flow pressure and time in the conventional animal urinary function measuring device 100. (4) of FIG. 7 is a graph showing the relationship between the measured water amount and time in the conventional animal urinary function measuring device 100. A point A of each of (1) and (3) of FIG. 7 indicates a water discharge start time point, while a point B of each of (1) and (3) of FIG. 7 indicates a water discharge termination time point. In addition, a point C of each of (2) and (4) of FIG. 7 indicates a water amount measurement start time point, while a point D of each of (2) and (4) of FIG. 7 indicates a water amount measurement termination time point. From FIG. 7, a water discharge rate of each of the animal urinary function measuring device 1 according to Embodiment 1 of the present invention and the conventional animal urinary function measuring device 100 is calculated.

In the animal urinary function measuring device 1 according to Embodiment 1 of the present invention, as shown in (1) and (2) of FIG. 7, the point A and the point C are substantially identical with each other, the point B and the point D are substantially identical with each other, an interval between A and. B and an interval between C and D are substantially identical with each other, and the water discharge amount by the syringe pump corresponded to the measured water amount measured by the measuring portion 8. Further, in the animal urinary function measuring device 1 according to Embodiment 1 of the present invention, as shown in (2) of FIG. 7, the measured water amount is obtained regularly stepwise so that it is possible to measure the water discharge amount on a real-time basis. Furthermore, in the animal urinary function measuring device 1 according to Embodiment 1 of the present invention, as shown in (2) of FIG. 7, the measured water amount of 0.40 mL was measured in 12.0 seconds. When the water discharge rate is calculated based on the values, the water discharge rate is 120 mL/hr, and the water discharge rate corresponds to the rate set in the syringe pump.

On the other hand, in the conventional animal urinary function measuring device 100, as shown in (3) and (4) of FIG. 7, there are time lags of about four seconds between the point A and the point C and between the point B and the point D, and an interval between A and B was 12 seconds, while an interval between C and D was 12.5 seconds. In addition, the discharge amount by the syringe pump was 0.40 ml, while the measured amount measured by the measuring portion 80 was 0.38 mL. Further, in the conventional animal urinary function measuring device 100, as shown in (4) of FIG. 7, the measured water amount is obtained irregularly stepwise so that the graph indicates that the water discharge amount is not reflected on a real-time basis. Furthermore, in the conventional animal urinary function measuring device 100, when the water discharge rate is calculated, the water discharge rate is 109 mL/hr, and the value is different from the set value of the syringe pump of 120 mL/hr so that it could be seen that the conventional animal urinary function measuring device 100 lacked accuracy.

From the above-described results, the animal urinary function measuring device 1 according to Embodiment 1 of the present invention is capable of measuring the water amount (the urine) without any loss on a real-time basis, and accurately measuring the urination rate. In particular, the animal urinary function measuring device 1 according to Embodiment 1 of the present invention has little influence of the adhesion to the reticulated portion 5 and the like, and hence it is useful for an animal having a relatively small urine amount and a test in which a urine amount used becomes small.

[Embodiment 2]

Figure 6A:
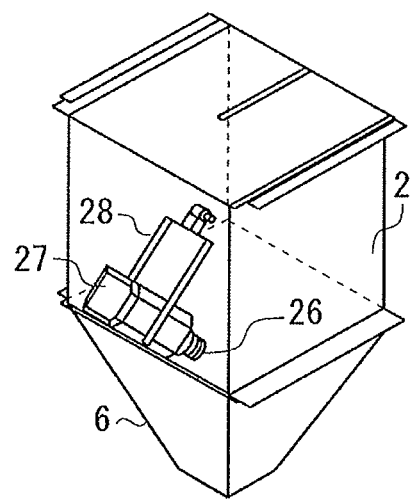
FIG. 6A is a perspective view showing an accommodating portion and an funneling portion in a conventional animal urinary function measuring device.
Figure 6B:
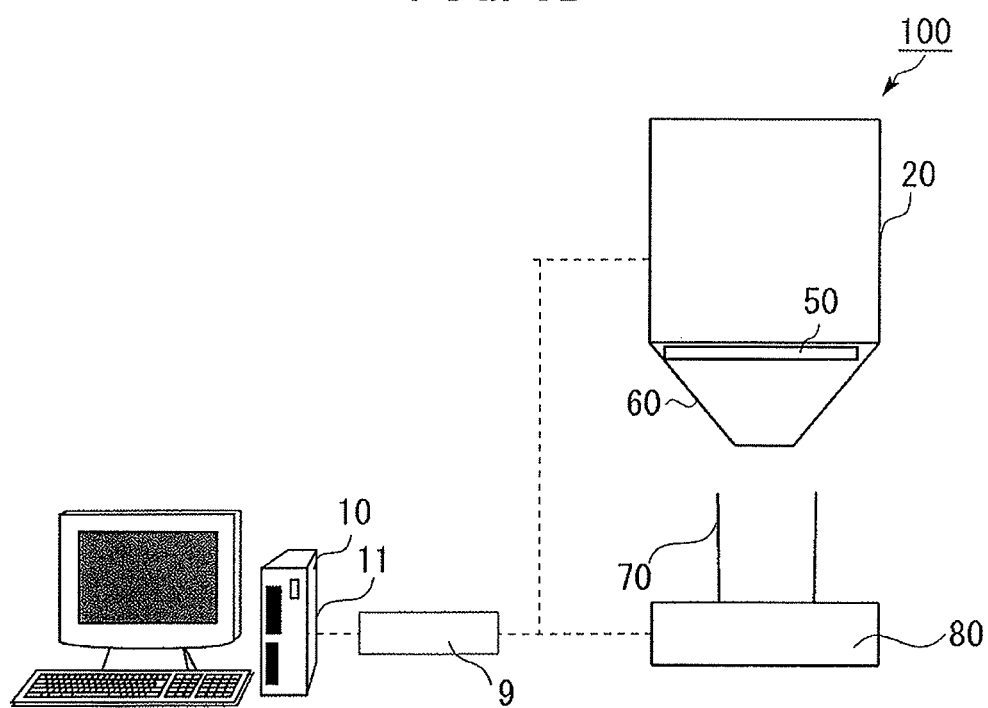
FIG. 6B is a schematic diagram showing the conventional animal urinary function measuring device.

Cystometry measurement using an animal urinary function measuring device 1 according to Embodiment 2 of the present invention and cystometry measurement using the conventional animal urinary function measuring device 100 are compared and examined. The animal urinary function measuring device 1 according to Embodiment 2 of the present invention is the same as the above-described animal urinary function measuring device according to Embodiment 1 of the present invention. As shown in FIGS. 6A and 6B, the conventional animal urinary function measuring device 100 is the same as that in animal urinary function measuring device 1 described in Embodiment 1 so that the description thereof is omitted.

An examination method is described. The animal urinary function measuring device 1 according to Embodiment 2 of the present invention and the conventional animal urinary function measuring device 100 use the same 12-week old SD rat (by CHARLES RIVER LABORATORIES JAPAN INC.). The cystometry measurement is conducted, the internal pressure of the bladder and the urine of the SD rat are analyzed, and the measurements are compared and examined based on the obtained values.

(1) of FIG. 8 shows the relationship between the bladder internal pressure of the SD rat and time in the animal urinary function measuring device 1 according to Embodiment 2 of the present invention. (2) of FIG. 8 shows the relationship between the measured urine amount measured by the measuring portion 8 and time in the animal urinary function measuring device 1 according to Embodiment 2 of the present invention. (1) of FIG. 9 shows the relationship between the bladder internal pressure of the SD rat and time in the conventional animal urinary function measuring device 100. (2) of FIG. 9 shows the relationship between the measured urine amount measured by the measuring portion 8 and time in the conventional animal urinary function measuring device 100. The presence or absence of the urination, a urination start time point, and a urination termination time point can be determined by the bladder internal pressure.

In the animal urinary function measuring device 1 according to Embodiment 2 of the present invention, as shown in FIG. 8, a rise in the value of the measured value is observed simultaneously with the urination start time point. In addition, the urination termination time point and the end of the periodic stepwise rise in the measured amount are concurrently observed, and it is possible to measure the urine amount from the urination start time point to the urination, termination time point on a real-time basis. With this, in the animal urinary function measuring device 1 according to Embodiment 2 of the present invention, it was found that the time point of the rise in the value of the measured amount might be determined as the urination start time point, and the end of the periodic stepwise rise in the measured amount might be determined as the urination termination time point. In addition, no adhesion to the animal urinary function measuring device 1 according to Embodiment 2 of the present invention, in particular, no adhesion to the reticulated portion 5 was observed, and no measurement loss was observed.

On the other hand, in the conventional animal urinary function measuring device 100, as shown in FIG. 9, an increase in measured amount was recorded about four seconds after the urination start time point, and the urination termination time point was recorded after the actual time point. In addition, the adhesion of the urine to the vicinity of the contact point between the reticulated portion 5 and the funneling portion 6 was observed.

From the above-described results, the animal urinary function measuring device 1 according to Embodiment 2 of the present invention is capable of accurate measurement of the urinary function on a real-time basis.

[Embodiment 3]

By using an animal urinary function measuring device 1 according to Embodiment 3 of the present invention, the urination rates of a young rat (10-week old) and an aged rat (26-month old) at the time of natural urination are compared and examined. The animal urinary function measuring device 1 according to Embodiment 3 of the present invention is the above-described animal urinary function measuring device according to the embodiment of the present invention.

An examination method is described. Five young rats (10-week old) and five aged rats (26-month old) are put in the accommodating portion 2 of the animal urinary function measuring device 1 according to Embodiment 3 of the present invention, the natural urination thereof is measured overnight, the urination rates are calculated on the basis of the obtained measured values, and the urination rates are compared and examined. From the urines of all of the five young rats accommodated in the accommodating portion 2, a urination point having a substantially identical urine amount is selected, the urination rates of the young rats are calculated, and the average urination rate of the five young rats is calculated. Similarly, the average urination rate of the five aged rats accommodated in the accommodating portion 2 is also calculated. The rats used in the test were purchased from CHARLES RIVER LABORATORIES JAPAN INC.

Each of (1) and (2) of FIG. 10 shows the relationship between the measured urine amount of each of two of the young rats and time Each of (3) and (4) of FIG. 10 shows the relationship between the measured urine amount of each of two of the aged rats and time.

The average value of the urination rate of the young rats is 0.22 mL/sec. The average value of the urination rate of the aged rats is 0.15 mL/sec. As a result, it was found that the urination rate of the rat was reduced by aging. In addition, it was observed that the aged rat suffered from pollakiuria, and it was suggested that the aged rat had the urination mode similar to that of humans.

From the above-described results, the animal urinary function measuring device 1 according to Embodiment 3 of the present invention is capable of grasping the health condition of the animal and the effect by the medication in detail.

<Modification>

Figure 11:
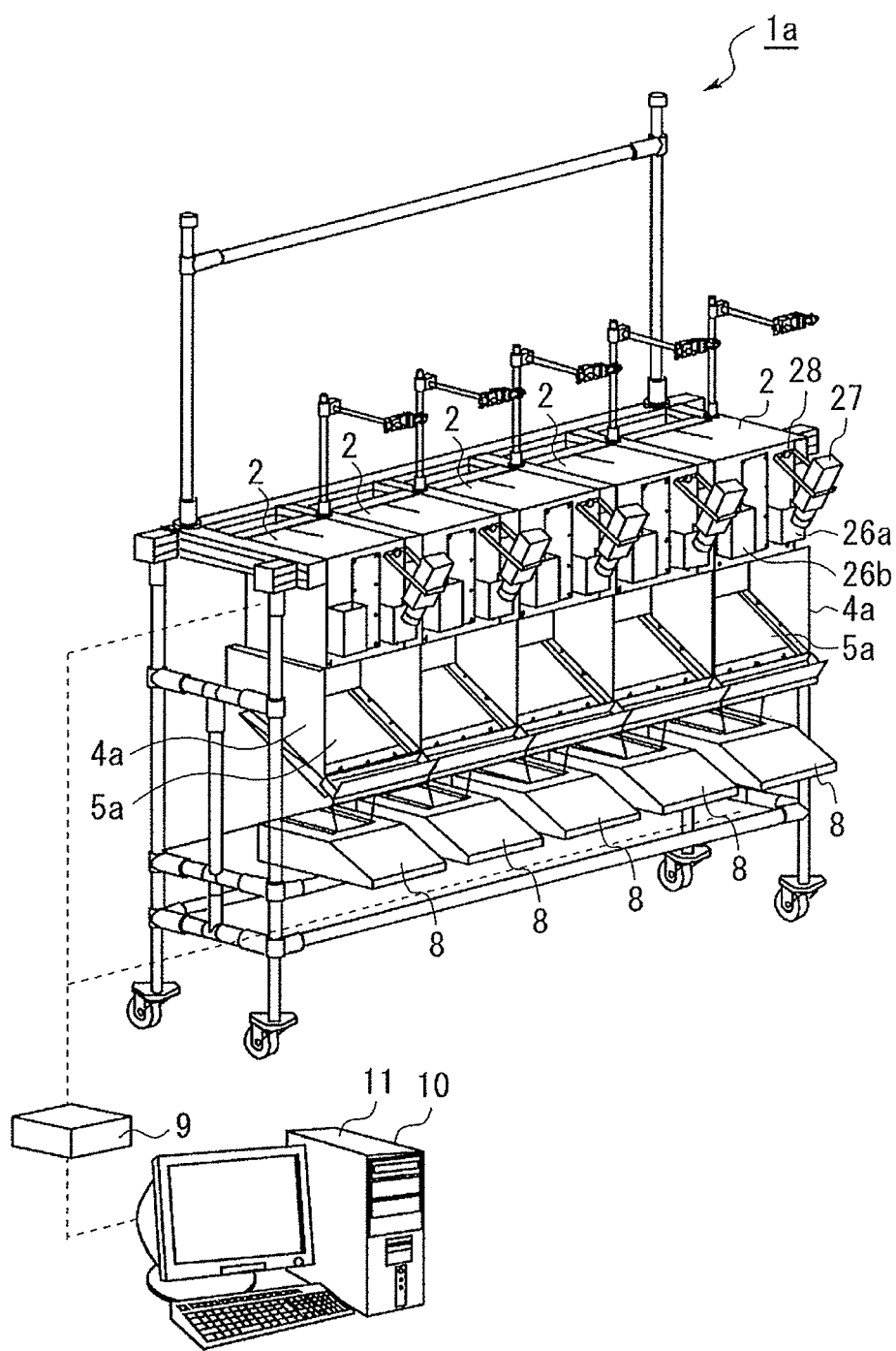
FIG. 11 is a perspective view when a plurality of animal urinary function measuring devices according to a modification are provided.
Figure 12:
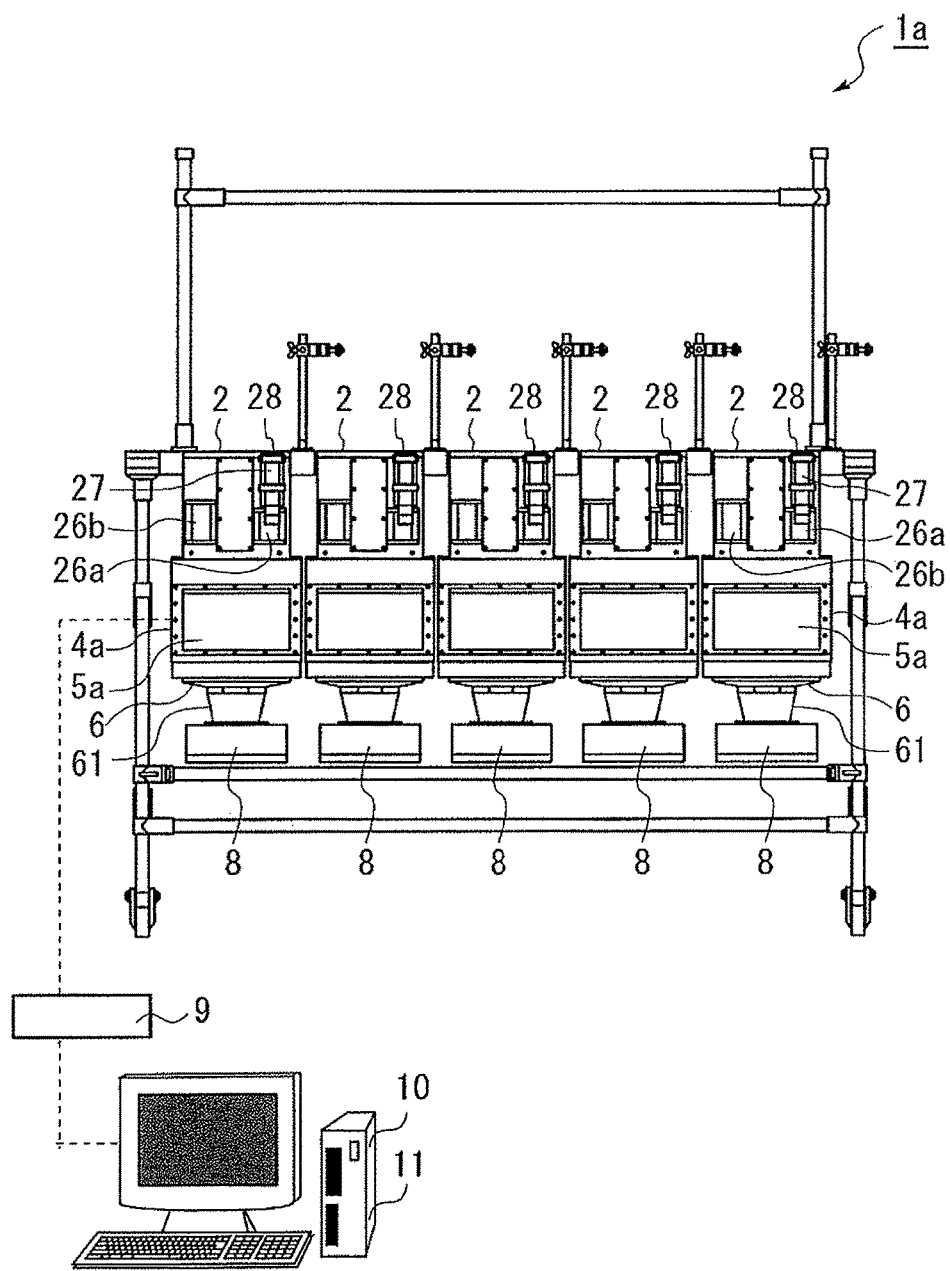
FIG. 12 is a rear view when a plurality of the animal urinary function measuring devices according to the modification are provided.
Figure 13:
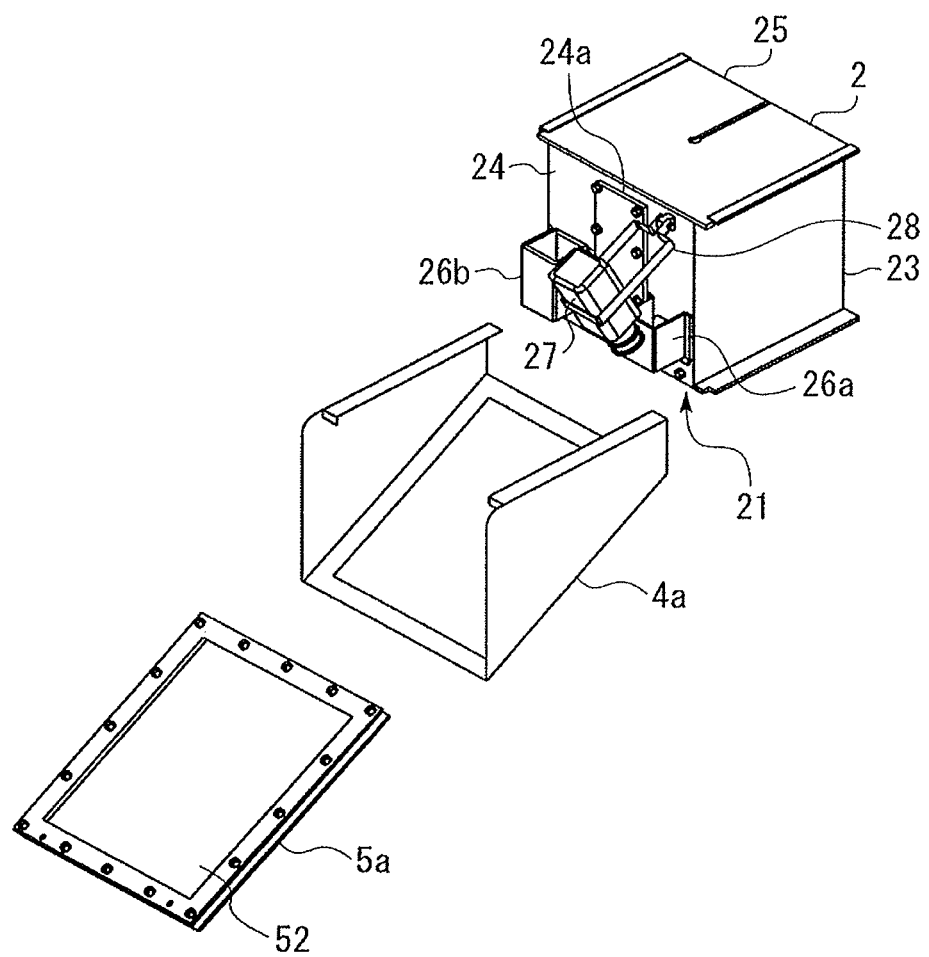
FIG. 13 is a schematic diagram showing a state where a reticulated portion is being installed in an accommodating portion in the animal urinary function measuring device according to the modification.
Figure 14:
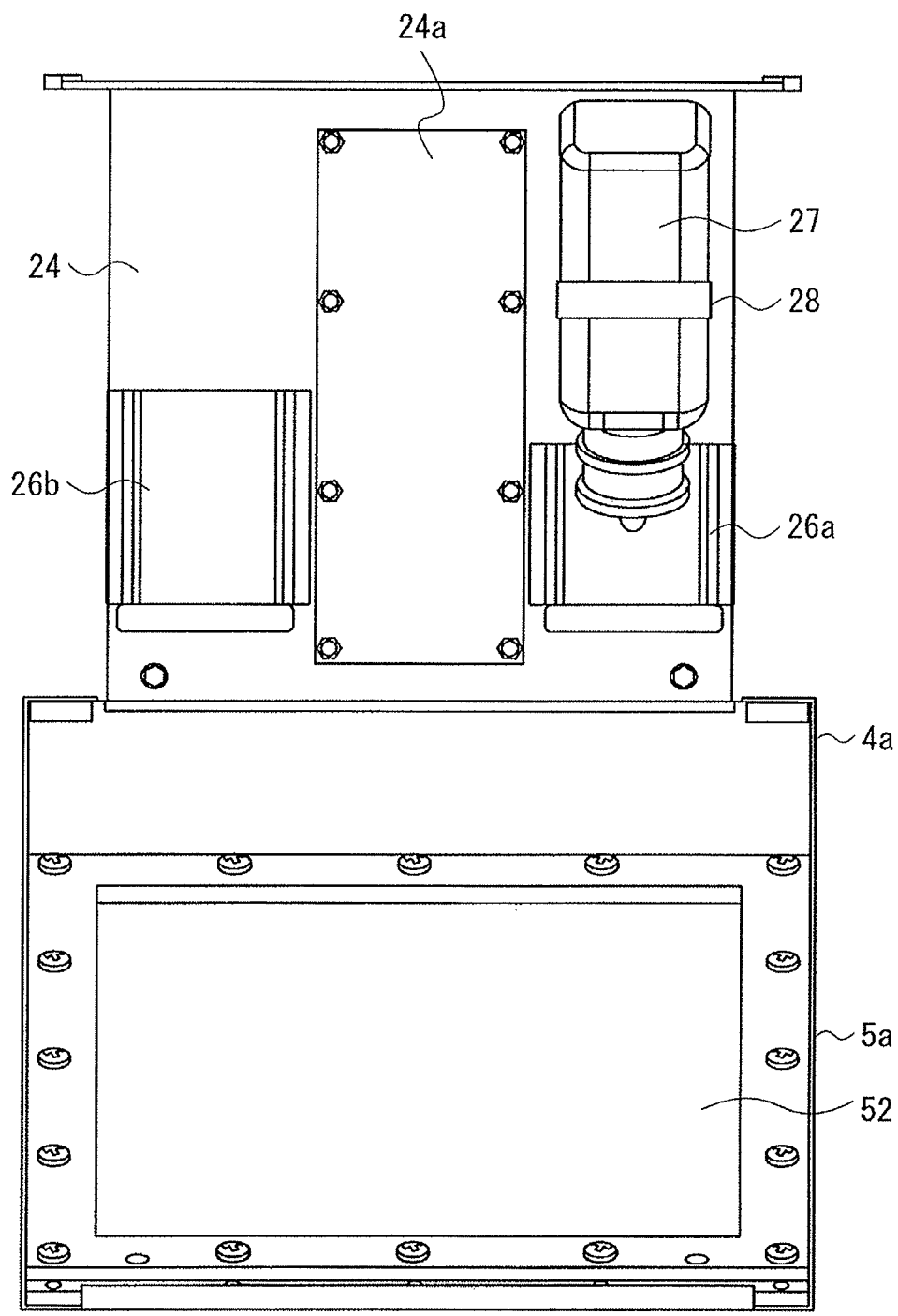
FIG. 14 is a rear view showing the state where the reticulated portion is installed in the accommodating portion in the animal urinary function device according to the modification.
Figure 15:
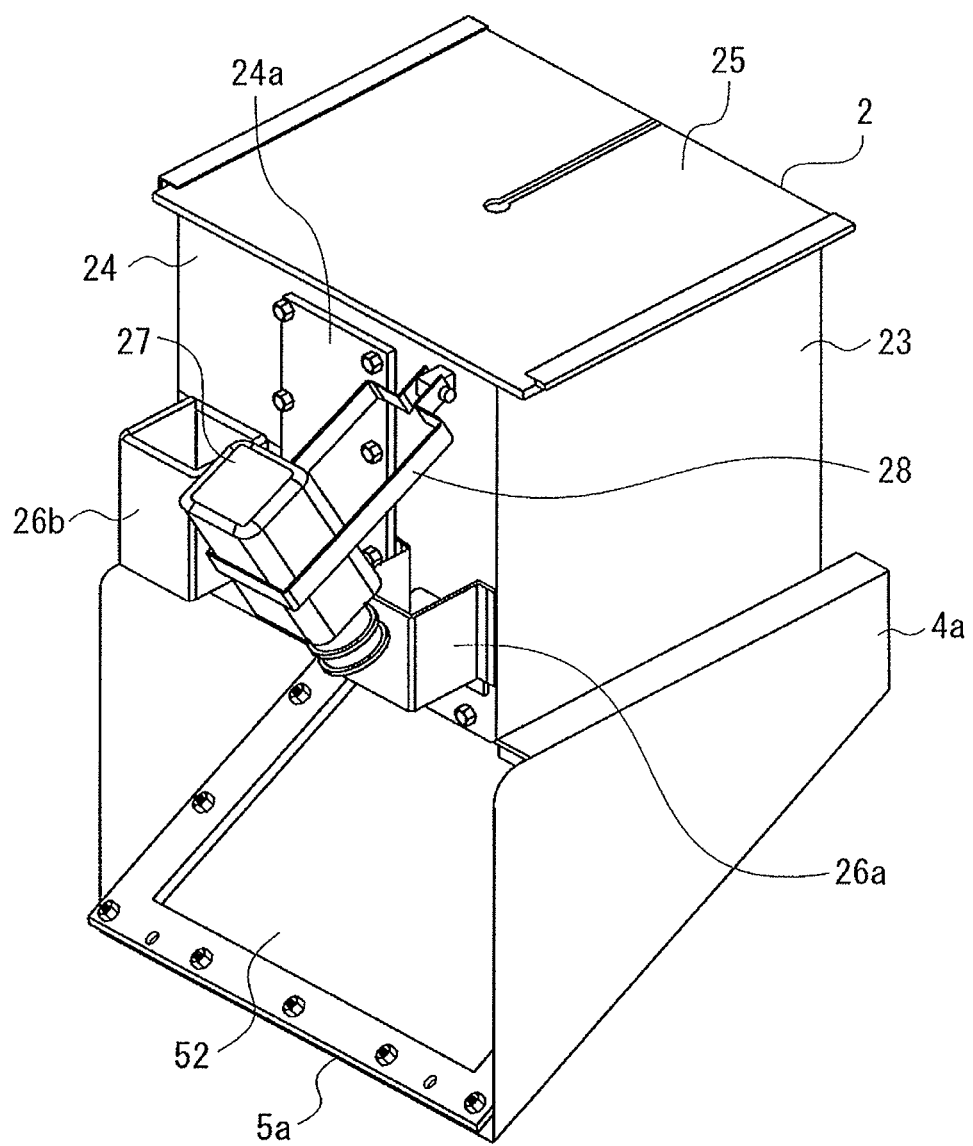
FIG. 15 is a perspective view showing the state where the reticulated portion is installed in the accommodating portion in the animal urinary function device according to the modification.

Next, a description is given of a modification of the above-described animal urinary function measuring device 1 according to the embodiment. FIG. 11 is a perspective view when a plurality of animal urinary function measuring devices according to the modification are provided. FIG. 12 is a rear view when the plurality of the animal urinary function measuring devices according to the modification are provided. FIG. 13 is a schematic diagram showing a state where a reticulated portion is being installed in an accommodating portion in the animal urinary function measuring device according to the modification. FIG. 14 is a rear view showing the state where the reticulated portion is installed in the accommodating portion in the animal urinary function measuring device according to the modification. FIG. 15 is a perspective view showing the state where the reticulated portion is installed in the accommodating portion in the animal urinary function measuring device according to the modification. Note that the components similar to those of the animal urinary function measuring device 1 according to the embodiment are designated with the same reference numerals, and the description thereof is omitted. Hereinbelow, differences from the animal urinary function measuring device 1 according to the embodiment are mainly described.

In an animal urinary function measuring device 1a according to the modification, a rectangular transparent plate 24a is provided in the center of the rear surface 24 of the accommodating portion 2. The area of the transparent plate 24a may be set to an area which does not affect the strength of the accommodating portion 2. The shape of the transparent plate 24a is not limited to the rectangular shape, and may be, e.g., a circular shape or a polygonal shape other than the rectangular shape. With the transparent plate 24a, a measurer can easily observe the state in the accommodating portion 2.

In addition, in the animal urinary function measuring device 1a according to the modification, a water supply opening 26a and a food opening 26b are provided in the outer surface of the rear surface 24 of the accommodating portion 2. By providing the water supply opening 26a and the food opening 26b outside the accommodating portion 2, when the animal drinks water or eats food, it is possible to reduce the possibility that the animal brings the water or food into the accommodating portion 2 by mistake. Consequently, the ingestion of water and food is allowed without hindering the measurement. Note that bags for collecting leftovers of water or food may be provided at the water supply opening 26a and the food opening 26b. With the bags provided, it is possible to easily perform cleaning, and keep the installation place of the animal urinary function measuring device 1a clean.

Further, in the animal urinary function measuring device 1a according to the modification, a reticulated portion 5a is installed obliquely relative to the bottom surface 21 of the accommodating portion 2. By installing the reticulated portion 5a obliquely, it is possible to gather objects other than the urine such as feces and food in the lower part where the urine does not pass. That is, the objects other than the urine such as feces and food which have dropped from above come in contact with the obliquely installed reticulated portion and the dropping direction is thereby changed, and hence it becomes possible to separate the urine from the feces and the food. As a result, it is possible to prevent a situation where the urine hits the feces or the food to disappear and the accurate measurement of the urine is thereby hindered. The installation angle of the reticulated portion 5a can be appropriately set according to the material of the reticulated portion 5a, the mesh size of the fine net portion 52, and the species of the animal used for the measurement as long as the objects other than the urine can be gathered in the lower part and the urine can pass through the mesh without difficulty. For example, the installation angle of the reticulated portion 5a is 10 degrees to 60 degrees, preferably 20 degrees to 40 degrees, and further preferably 30 degrees. As for the mesh size, the mesh size when the obliquely installed reticulated portion 5a is viewed from immediately above may appropriately be identical with the mesh size of the above-described animal urinary function measuring device 1a according to the embodiment.

Note that, in the case where the reticulated portion 5a is installed obliquely relative to the bottom surface 21 of the accommodating portion 2, the bottom surface 21 and the reticulated portion 5a are desirably installed independently of each other. Further, it is desirable that the feces of the animal and a predetermined object (e.g., food) used to accommodate the animal can be quickly removed from the bottom surface 21 because the possibility that the collection of the urine is hindered is reduced. Consequently, the bottom surface 21 may simply be capable of allowing the passage of the excrement of the animal and the predetermined object, and the excrement of the animal and the predetermined object may be appropriately gathered in the lower part where the urine does not pass by the obliquely installed reticulated portion 5a.

Although the preferred embodiments of the present invention have been described thus far, the animal urinary function measuring device according to the present invention is not limited thereto, and can include all possible combinations thereof.

CROSS-REFERENCE TO RELATED APPLICATIONS

This application is based upon and claims the benefit of priority of the prior Japanese Patent Application No. 2009-187420, filed on Aug. 12, 2009, the entire contents which are incorporated herein by reference.

The invention claimed is:

1. An animal urinary function measuring device comprising:
   an accommodating portion which accommodates an animal other than a human;
   a collecting portion which is provided below the accommodating portion and collects urine discharged by the animal in the accommodating portion;
   a reticulated portion which is provided between the accommodating portion and the collecting portion, allows passage of the urine of the animal into the collecting portion, collects an object other than the urine, and whose wire diameter of a net thereof being 0.1 mm or less and whose mesh size being not less than 1 $mm^2$ and not more than a maximum mesh size determined by at least one of excrement of the animal accommodated in the accommodating portion and a predetermined object used to accommodate the animal in the accommodating portion;
   a measuring portion which measure a weight of the urine collected by the collecting portion;
   a funneling portion which is provided between the reticulated portion and the collecting portion that has a shape having an open upper part and a narrow lower part and funnels the urine discharged by the animal in the accommodating portion into the collecting portion;
   a funneling portion holding portion which is provided on the measuring portion and which is provided in contact with the measuring portion and which supports the funneling portion from below; and
   a data recording portion which records data measured by the measuring portion,
   wherein the reticulated portion is a portion different from a bottom surface of the accommodating portion,
   wherein the reticulated portion is provided below the bottom surface of the accommodating portion and provided above the collecting portion, and
   wherein the funneling portion holding portion and collection portion are different members.

2. The animal urinary function measuring device according to claim 1, further comprising a reticulated portion attaching/detaching portion which is provided below the accommodating portion and is capable of attaching and detaching the reticulated portion.

3. The animal urinary function measuring device according to claim 1, further comprising a urination rate calculating portion which calculates a rate of urination based on the data recorded by the data recording portion.

4. The animal urinary function measuring device according to claim 1, further comprising a second accommodating portion which has a size matching an activity area of the animal in the accommodating portion.

5. The animal urinary function measuring device according to claim 1, wherein the reticulated portion is provided obliquely relative to the bottom surface of the accommodating portion.

6. An animal urinary function measuring method which measures a urinary function of the animal by using the animal urinary function measuring device according to claim 1.

7. The animal urinary function measuring device according to claim 1, wherein the wire diameter of the net is 0.03 mm or less.

8. The animal urinary function measuring device according to claim 7, wherein the mesh size of the net is about 1 $mm^2$.

9. The animal urinary function measuring device according to claim 7, wherein the mesh size of the net is about 2 $mm^2$.

10. The animal urinary function measuring device according to claim 1, wherein the wire diameter of the net is 0.06 mm or less.

11. The animal urinary function measuring device according to claim 1, wherein the mesh size of the net is about 1 $mm^2$.

12. The animal urinary function measuring device according to claim 1, wherein the mesh size of the net is about 2 $mm^2$.

13. The animal urinary function measuring device according to claim 1, wherein a bottom surface of the collecting portion is provided in contact with the measuring portion.

* * * * *